United States Patent [19]

Stevenson

[11] Patent Number: 5,093,115
[45] Date of Patent: Mar. 3, 1992

[54] METHOD OF PREPARING ACTIVATED KILLER MONOCYTES FOR TREATING COLORECTAL CANCER

[75] Inventor: Henry C. Stevenson, Kensington, Md.

[73] Assignee: The United States of America as represented by the Department of Health & Human Services, Washington, D.C.

[21] Appl. No.: 209,108

[22] Filed: Jun. 20, 1988

Related U.S. Application Data

[63] Continuation-in-part of Ser. No. 743,570, Jun. 11, 1985, abandoned.

[51] Int. Cl.$^5$ ..................... A61K 37/66; A61K 45/05
[52] U.S. Cl. ................................. 424/85.5; 424/85.1; 424/85.4
[58] Field of Search ..................... 424/85.1, 85.4, 85.5

[56] References Cited

PUBLICATIONS

Kornbluth et al., "Alymphokine Cofactor . . . ", Federation Proc. 44(5): 1699 #7533 Abst. (1985).
Wudarski et al., "Monocytes . . . ", Federation Proc. 44(5): 1700 #7541 Abst. (1985).
Stevenson et al., 1984, Journ. of Immun. Methods, 70:245-255.
Le et al., Journ. of Immun., 131:2821-2826.
Stevenson et al., 1984, Plasma Ther Transfus Technol, 5:237-50.

Primary Examiner—Frederick E. Waddell
Assistant Examiner—Gregory Hook
Attorney, Agent, or Firm—Mishrilal L. Jain

[57] ABSTRACT

The present invention discloses a method of preparing activated killer monocytes for treating colorectal cancer. Activated killer monocytes are prepared in serum free medium in polypropylene containers.

2 Claims, 6 Drawing Sheets

FIG.2

FIG.6A
FIG.6B
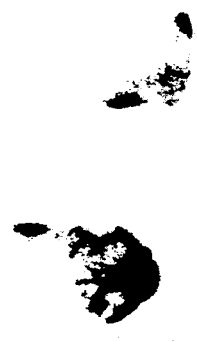
FIG.7A
1 HOUR — ANTERIOR ABDOMEN / POSTERIOR CHEST
24 HOURS — ANTERIOR ABDOMEN / POSTERIOR CHEST
FIG.7B
FIG.7C
48 HOURS — ANTERIOR ABDOMEN / POSTERIOR CHEST
5 DAYS — ANTERIOR ABDOMEN / POSTERIOR CHEST
FIG.7D

METHOD OF PREPARING ACTIVATED KILLER MONOCYTES FOR TREATING COLORECTAL CANCER

This is a continuation in part of the application Ser. No. 06/743,570 filed June 11, 1985, now abandoned.

TECHNICAL FIELD

The present invention is related generally to cancer therapy. More particularly, the present invention is related to monitoring in cancer patients the tumoricidal activity of purified human monocytes cultured in suspension in a serum-free medium.

BACKGROUND OF THE INVENTION

Mononuclear phagocytes (monocytes) in their various forms have been shown to participate in many critical phases of the mammalian immune response. Monocytes and macrophages are known to be essential for the initiation of immune responses by virtue of their ability to process antigen (Rosenthal, New Engl. J. Med. 303, 1153. 1980), and for their ability to secrete soluble factors such as interleukin 1 (IL-1), colony stimulating factor (CSF), interferon (IFN) and prostaglandin E (PGE) which allow them to function as immunoregulators for a number of immune responses (Epstein, Biology of Lymphokines; Academic Press, NY, pp. 123-152. 1979; Stevenson, The Reticuloendothelial System. A Comprehensive Treatise, Vol. VI: Plenum Press, NY, pp. 79-91. 19882). In addition, monocytes are known to play critical role as final effector cells in humoral immunity by virtue of the fact that these cells secrete complement components (Nathan, et al, New England J. Med. 303, 623. 1980) and are capable of mediating cytotoxic functions. In addition to antibody-dependent cellular cytotoxicity (ADCC) (Poplack, et al, Blood 48, 890. 1976), activated killer monocytes (AKM) are known to be potent killers of tumor cells (Stevenson, et al, Artificial Organs 112, 128. 1988).

Assessment of the in vitro function of human monocytes and AKM has been hampered by a number of technical and theoretical problems. First, monocytes constitute a very low proportion of the cells in human peripheral blood (generally less than 5%); thus, obtaining large numbers of them has been quite difficult. In addition, very few techniques have emerged which allow for the large-scale isolation of purified populations of human monocytes by negative selection; instead, generally small numbers of rather impure monocytes are isolated on gradients such as Percoll (Hester, et al., 1981) or cells of higher purity are obtained by adhering them onto plastic or glass labware by positive selection (Werb, J. Exp. Med. 147, 1695. 1978).

When monocytes are obtained by positive selection, it is difficult to remove them for further study; a variety of rather harsh measures are utilized to remove the adhered cells from the plastic or glass surface, ranging from the use of rubber policemen (Pennline. Manual of Macrophage Methodology, pp. 65-77. 1981), EDTA (Ackerman and Douglas, J. Immunol. 120, 1372. 1979), and lidocaine-containing solutions (Koski, et al, In Vitro Methods in Cell-Mediated and Tumor Immunity, Academic Press, p 359. 1976). The potential problems of adherence and positive selection are compounded when the cells are activated in culture into AKM since most researchers employ some sort of polystyrene labware to which the monocytes will readily adhere.

Adherent monocytes, of course, are in a different condition from their normal state of suspension in human peripheral blood. Therefore, the functions may also be different. Furthermore, when placed in medium conditions under which they are generally cultured, human monocytes demonstrate a number of technical inadequacies. These problems mainly stem from the limited nutrients provided in most standard laboratory culture media for a cell as metabolically active as the human monocyte, and the additional potential artifacts created by culturing human monocytes with sera from different human individuals (AB serum) or from other species (such as fetal calf serum). Thus consistent and uniform conditions for culturing human monocytes and transforming them into AKM cannot be assured from batch to batch.

The above-cited problems regarding the handling of human monocytes are compounded when these cells are transformed into activated killer monocytes (AKM) for the treatment of cancer. Prior to the present invention, it has not been possible to prepare AKM in suspension suitable for administration to cancer patients for therapy. Moreover, no method for monitoring the cytotoxic activity of serum-free, suspension cultured AKM in vitro existed.

SUMMARY OF THE INVENTION

It is, therefore, an object of the present invention to provide substantially pure, clinical grade, functional, human, AKM produced in suspension in polypropylene were in a serum free medium.

It is a further object of the present invention to provide an assay for monitoring the tumorical function of isolated, substantially pure, human monocytes cultured in suspension in serum-free medium and transformed into activated killer monocytes (AKM).

It is an additional object of the present invention to provide a method of treating cancer in mammals comprising administering to said mammal an immunotherapeutic amount of isolated, purified monocytes suspended in a serum-free medium and transformed into AKM with suitable adjuvants and/or biological response modifiers.

Other objects and advantages of the present invention would become apparent from the following detailed description of the invention.

BRIEF DESCRIPTION OF THE DRAWINGS

These and other objects, features and many of the attendant advantages of the invention will be better understood upon a reading of the following detailed description when considered in connection with the accompanying drawings wherein:

FIG. 2 is a scanning electron micrograph showing superior killing interactions between AKM (▲) and tumor target cells (↑) in vitro under polypropylene (C&D) versus polystyrene (E&F) culture conditions.

FIG. 6 (A-B) and 7 (A-D) show the distribution of $^{111}$Indium-labeled AKM in the peritoneum 4 hours after infusion into a peritoneal colorectal carcinomatosis patient.

DETAILED DESCRIPTION OF THE INVENTION

Figure 1:
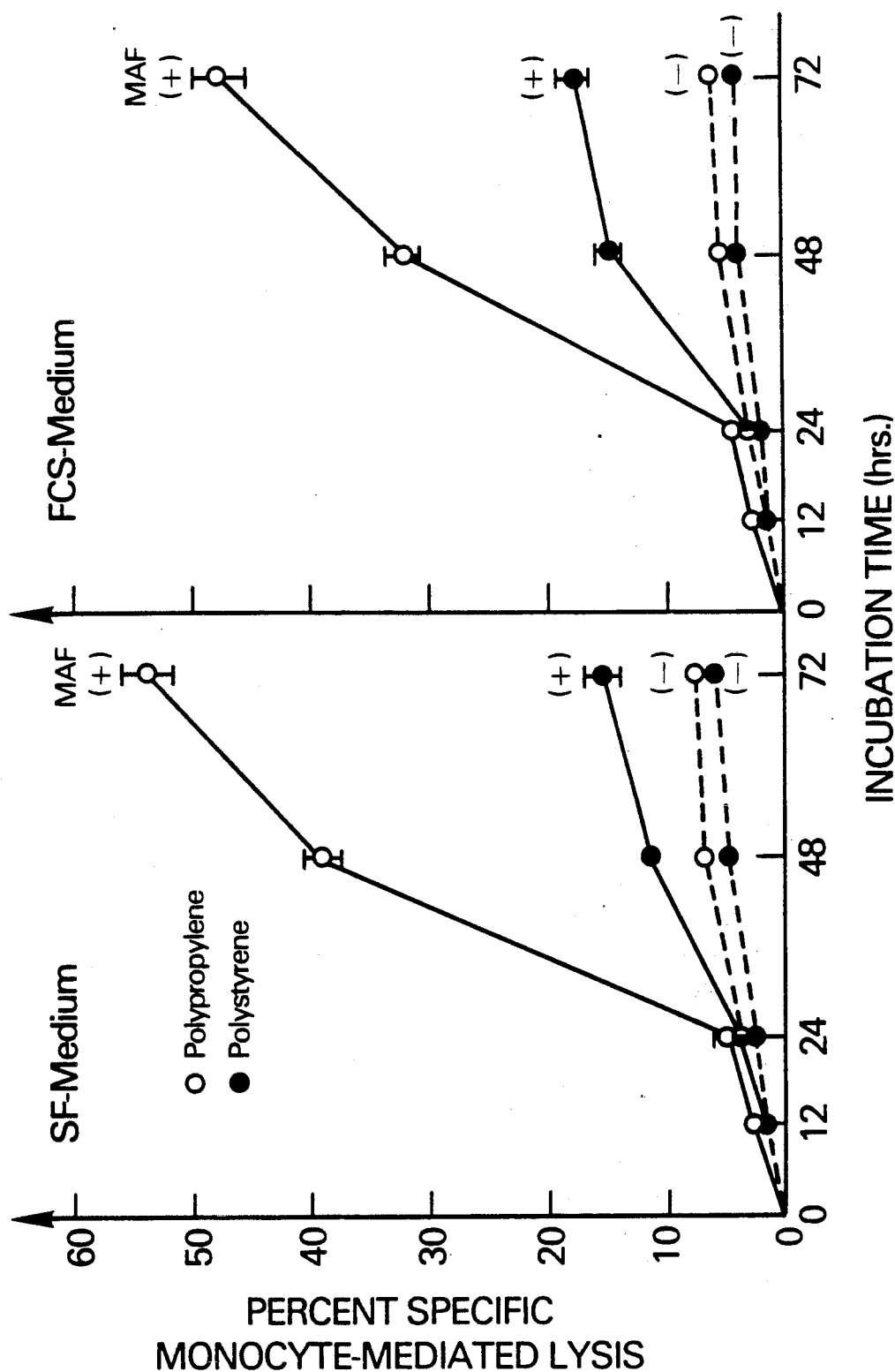
FIG. 1 displays the enhanced tumor cell killing capability of AKM cultured under serum-free and suspension culture conditions.

These and other objects and advantages of the present invention are achieved by providing isolated, substantially pure clinical grade, functional, human monocytes produced in suspension in polypropylene wares in a sterile, serum-free medium and activated with biological response modifiers and/or adjuvants into AKM and monitoring their tumoricidal activity in vitro.

An important aspect of the present invention is the use of such apparatus, containers, appliances, laboratory equipments and the like that are made of a material which is inert or non-toxic to the human monocytes and to which the human monocytes do not adhere or stick. The use of non-toxic, non-adherent wares throughout the manipulative steps, in any manner related to the handling of human monocytes, is a critical feature of the present invention. A preferred example of an inert, non-toxic, non-adherent and sterilizable material which can be suitably employed in accordance with the present invention is polypropylene. Other similar or equivalent materials, other than polytetrafluoroethylene, can, of course, be also used so long as such material is non-toxic and non-adherent to the human monocytes and clinical grade AKM can be produced.

The containers, in accordance with the present invention, are made out of solid polypropylene sheets. Some examples of such containers or laboratory wares are flasks and micro titer plates and the like of various shapes and sizes, preferably ranging from 0.1 to 200 ml capacity. For convenience, of course, the shapes and sizes of solid polypropylene containers are chosen to be similar to other laboratory wares routinely used for testing, culturing or other preparative work.

The term "substantially pure" or "substantially purified" as used herein means that the human monocytes are as pure as it is possible to obtain by standard techniques and methods commonly known to one of the ordinary skill in the art to which this invention pertains. However, a purity of 90 percent or greater is necessary for the monocytes to be substantially pure.

The term "activated killer monocytes" or AKM as used herein means that the isolated monocytes have been exposed to or treated with such agents or factors which would stimulate, modify or enhance the immunoregulatory, biological or physiochemical property, native characteristics or functions of the monocytes. Such agents or factors include suitable antigens, adjuvants, biological response modifiers (BRMs) and the like.

The term "inert" container as used herein means that the material of which said container is made has no deleterious or toxic effect on the natural or normal functions of the monocytes cultured in said container. Polypropylene containers are specifically preferred in this invention for obtaining clinical grade AKMs. It is noted that Teflon, which has been suggested by the prior art, is unsuitable for the preparation of clinical grade AKMs in sufficient amounts (data not shown) in accordance with the present invention.

The term BRMs include a diverse spectrum of compounds including natural cytokines such as interferons (IFN), lymphokines such as interleukin-1 (IL-1), certain synthetic chemicals with immunomodulatory properties such as polyriboinosinic acid, polyribocytidylic acid, poly L-lysine, carboxymethylcellulose, (poly ICLC) and levamisole; immunomodulatory adjuvants such as Bacille Calmette Guerin (BCG), *Corynebacterium parvum*, Staphylococcus protein A, monoclonal antibodies, tumor antigen preparations and the like. Colony stimulating factors (CSF) and prostaglandin E (PGE) are other examples of suitable BRMs.

Human monocytes can be isolated from the peripheral blood following routine techniques well known in the art. However, the preferred methods and materials employed for isolation and purification of the monocytes are described hereunder. Other preferred methods and materials utilized are also described. All publications cited hereunder are incorporated herein by reference.

Isolation of human monocytes

Leukocytes were obtained by leukapheresis (Celltrifuge II leukapheresis apparatus, Travenol Laboratories, Deerfield, Ill.). Monocytes are then purified from the unfractionated mononuclear leukocyte preparation by counter-current centrifugation elutriation (CCE) (Stevenson and Fauci. Manual of Macrophage Methodology; Marcel Dekker, NY. pp. 74–80. 1981). The purity and viability of the monocyte preparations are then determined by nonspecific esterase staining, Wright's staining, and latex bead ingestion as described by Stevenson and Fauci, supra. The average yield of monocytes per normal donor was about 550 million cells (Stevenson, et al. J. Immunol. Meth. 62, 353. 1983).

Culture technique

New culture techniques were developed to allow for maintenance of the single-cell suspension state of purified human monocytes, utilizing specially developed culture plates made of polypropylene. These culture plates match the exact dimensions of standard 24-well flat-bottomed and 96-well round-bottomed polystyrene culture plates (Costar Plastics, Cambridge, Mass.). Human monocytes are counted with an automated cell counter (Electrozone/Celloscope, Particle Data, Elmhurst, Ill.) and suspended in serum-free medium or (Roswell Park Memorial Institute, Buffalo, N.Y.) RPMI 1640+10% human serum+L-glutamine at a concentration of 106 monocytes/ml. For those studies in which human serum was employed, no improvement of AKM function was noted when concentrations in excess of 10% were utilized; therefore, 10% human AB in RPMI 1640 serum was used as the standard serum-containing medium. The serum-free media employed was as described by Stevenson, et al (T. Immund. Meth. 65, 129, 1983) except that beta-mercaptoethanol, which is cytotoxic in vivo, was omitted. No antibiotics were added to the cell culture suspension. Activators of AKM include: Interleukin-2 (IL2) (Cetus), gamma interferon (ISNY) (Genentech) in ranges of 1–1000 units/ml and polyriboinosinic acid polyribocytidylic acid (poly I:C) (Sigma) in ranges of 10–200 mg/ml. Suspension monocyte cultures were placed at 37° C. in a 5% $CO_2$ incubator either in polypropylene or polystyrene labware. Maximal levels of killing of Indium-111 labelled human tumor targets were found at 48–72 h of culture, at which time the plates were spun once at 200×g and the cell culture supernatant was harvested for subsequent determination of Indium-111 release. All cultures were performed in triplicate.

Percent (%) release (AKM tumor cell killing) was calculated according to the following equation: 100(A/T), where A=cpm released from test well and T-total cpm incorporated into cells. Spontaneous release is % release when target cells alone were incubated. Percent specific AKM-mediated cytotoxicity was obtained by the following equation, 100(B-C)/(T-C), where B=cpm released from test well containing monocytes and targets in presence or absence of stimulants (C=cpm released from test well containing targets alone in presence or absence of the same stimulant as B). Although C was almost identical to spontaneous release, it was monitored in every experiment; C never exceeded 25%. Lytic unit calculations were performed as previously described (Stevenson, et al. Am. J. Hematol. 22, 123, 1986).

Statistical methods

For each of the experiments, a linear statistical model which includes all of the main variables (plate type, medium type, and activating agents) along with main variable interactions was employed. Analysis of variance was performed on the raw cytotoxicity data to determine significance of main effects. For factors of more than 2 levels, Duncan's multiple range test was employed to determine significance of pairwise differences (Snedecor and Cochran, Statistical Methods, pp. 233-237. 1980).

Effect of culture system variables on AKM tumoricidal activity

The effects of serum-free versus AB serum and polystyrene versus polypropylene culture plates are summarized in FIG. 1. Serum-free medium was shown not to significantly affect the baseline level of tumoricidal activity in either the adherent (polystyrene) or the suspension (polypropylene) culture systems. In contrast, serum-free medium significantly enhanced AKM tumor cell killing when optimal doses of activating agents were used ($P=0.03$).

Figure 3:
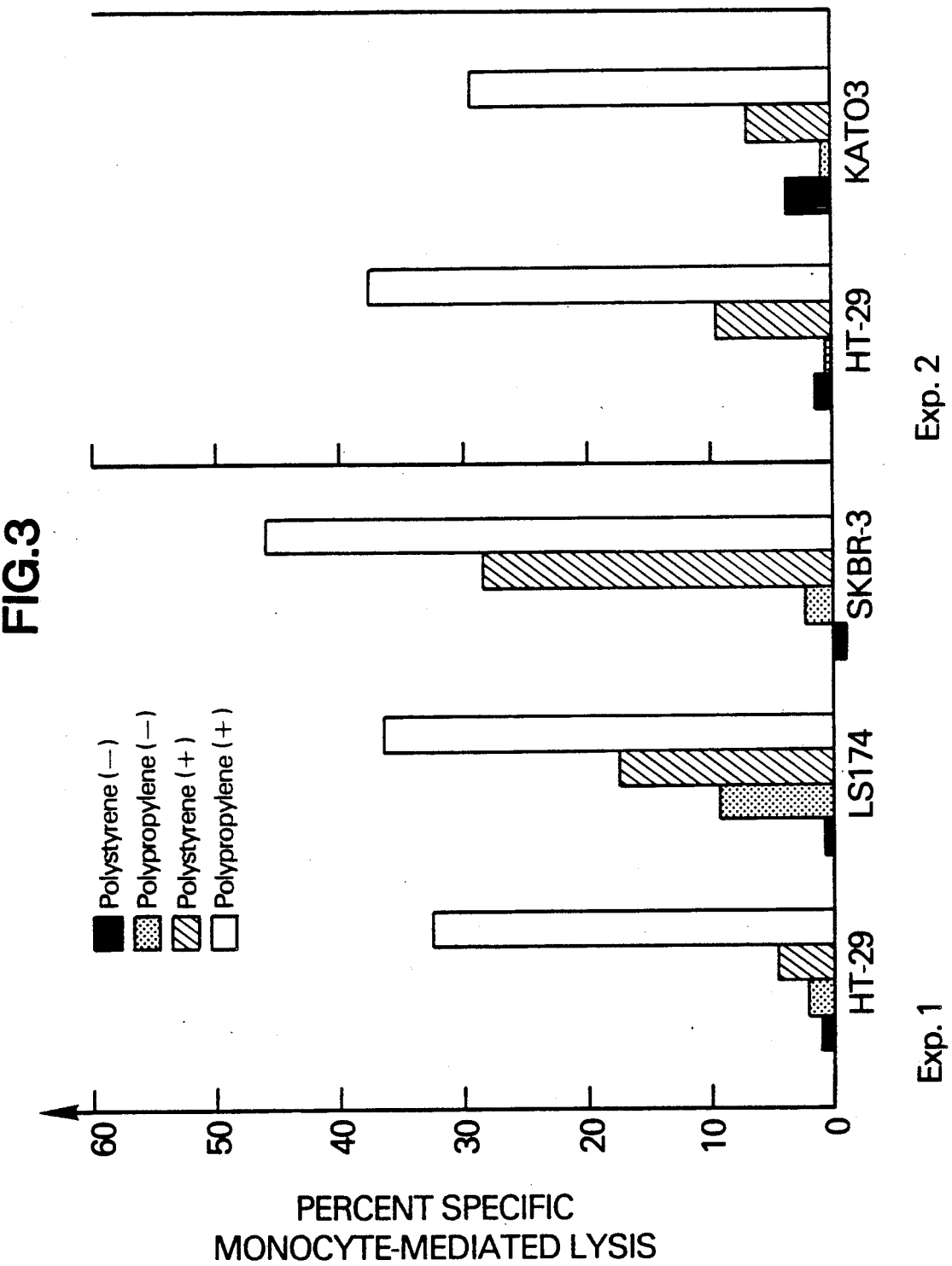
FIG. 3 shows enhanced effectiveness of AKM killing of a variety of human tumor targets under polypropylene versus polystyrene culture conditions.
Figure 4:
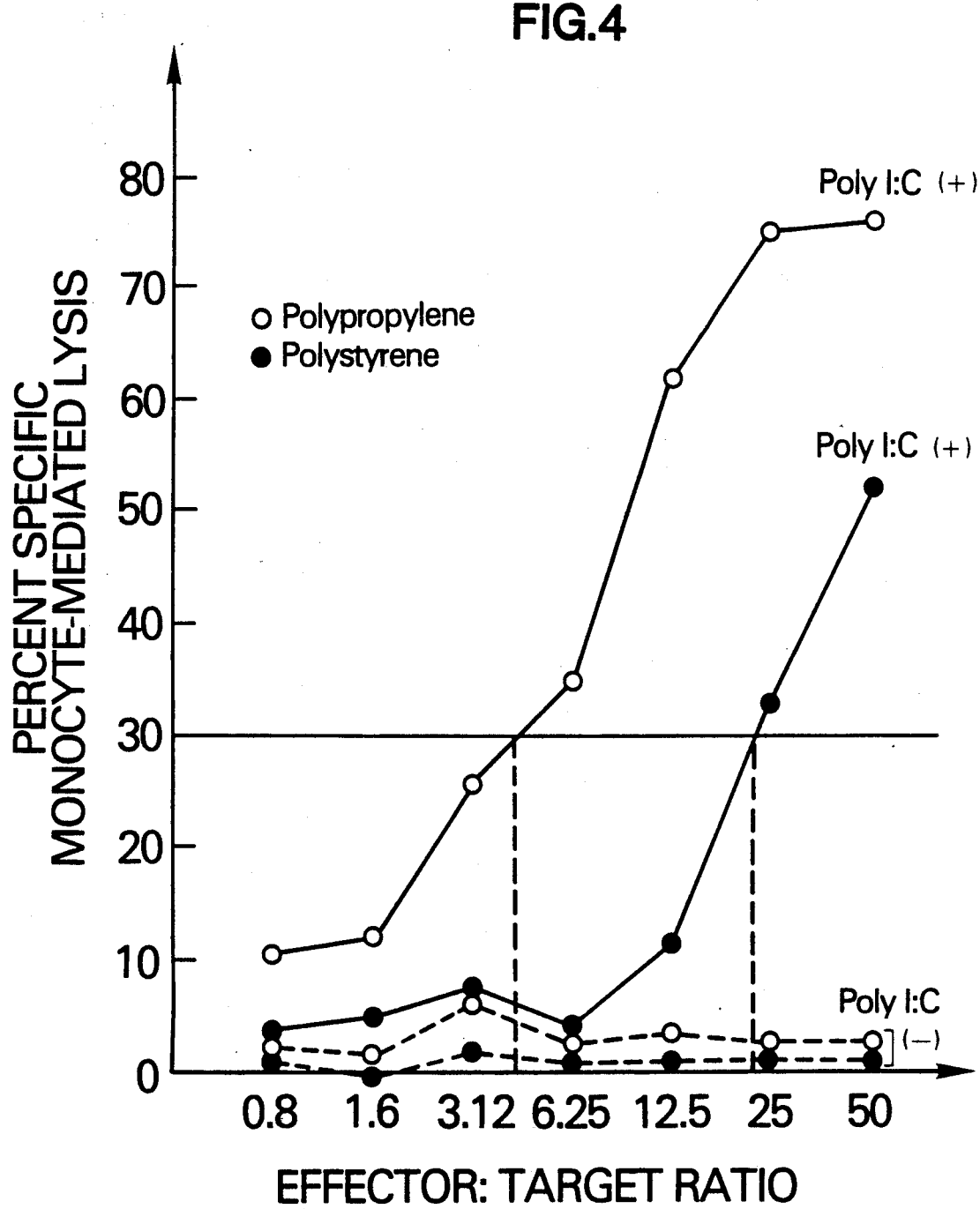
FIG. 4 shows the first representation of tumor cell killing by AKM depicted by the lytre unit method, an achievement possible only under serum-free suspension culture conditions of the present invention.

It is to be noted that AKM displayed significantly more tumor cell killing capacity in the polypropylene culture plates ($P<0.001$) as compared to polystyrene plates under both AB and serum-free conditions. This is demonstrated by FIG. 2 which shows enhanced attack of tumor targets by AKM in polypropylene (C) as compared to polystyrene (E) plates; actual killing of targets by AKM is also seen in polypropylene (D) versus polystyrene (F) plates. The enhanced killing capacity of AKM monitored in the described serum-free suspension culture technique was shown to be applicable to a wide range of human tumors (HT-29, LS 174, SKBR3 and KA(0-3) (FIG. 3). This in vitro technology for generating and monitoring the tumoricidal function of AKM has allowed the expression of cytotoxicity data for the first time by the lytic unit method, a data display technique previously only applicable to the killing of tumor cells by lymphocytes. As shown in FIG. 4, this achievement has now been possible because of the enhanced reproducibility and dose-response (effector to target ratio) curve data only afforded by the serum-free, suspension culture technology in polypropylene wares.

AKM Therapy of Human Cancer

The object of AKM therapy is to remove substantial numbers of leukocytes from the peripheral blood or bone marrow of cancer or immune dysfunction patients, followed by the purification of certain cytotoxic leukocyte subsets. Such purified leukocytes are then expanded and/or activated to tumoricidal or immunotherapeutic activity in vitro followed by reinfusion of these cells into the sites of tumor burden or immune dysfunction in the patient.

Several clinically relevant criteria must be considered in the design of any AKM protocol. As shown in Table I, it is important to employ a single, purified, sterile, toxic-free, cytotoxic leukocyte subset that is capable of being used in a clinical setting (this includes being not only sterile but devoid of any toxins). The use of purified leukocyte subsets allows for precise toxicity and physiologic determinations for each cell type. In the event that the administration of a single cell type is not ameliorative or curative of the immune dysfunction then one can build upon the single cell type baseline clinical data to design rational "combination activated leukocyte" protocols.

It is important that s sufficient number of cells be obtained to produce a clinical effect when infused into the patients (at least 500 million). It is also essential that these cells be maintained in a state of suspension to avoid the clinical problems encountered when trying to infuse clumps of cells. Leukocyte activating substances must be of clinical grade. Until graft-versus-host disease problems have been clinically minimized, it is preferred that EVLA protocols are restricted to the use of autologous leukocytes. A further consideration is that if in vitro testing demonstrates that the patient's leukocytes have activity against his or her tumor cells, mechanisms must be devised to allow for "homing" of the cytotoxic leukocytes to the sites of tumor burden in the patient.

TABLE I

| Desirable Attributes of AKM Therapy Protocol. |
| --- |
| A. A single purified cytotoxic effector cell should be employed. |
| B. Should be able to purify effector cells in a manner that allows cells to be used clinically (i.e., pyrogen, pathogen and toxin-free). |
| C. If amplifying and/or activating substances are employed, they should be purified and of clinical grade (IND # required). |
| D. FDA will require a separate approval for the "activated effector cell" prior to patient use. |
| E. Cells should be capable of being cultured in suspension—in absence of antibiotics, animal sera or any other sensitizing agents. |
| F. Mechanism for obtaining enough effector cells to elicit clinical response and/or toxicity should be identified. |
| G. Autologous cells should be employed until graft-vs-host disease problem is solved. |
| H. Mechanism for homing effector cells to tumor site must be identified. |
| I. In vitro testing should demonstrate activity of purified effector cells against patient's tumor cell type. |

AKM Protocol for Peritoneal Colorectal Carcinomatosis

As mentioned herein supra, a great number of the immunologic effector cell functions of monocyte/macrophage cell types have been characterized including antigen presentation, the production of certain immunoregulatory biological response modifiers such as alpha interferon, interleukin 1, colony stimulating factor, and certain critical components of the complement system. Monocytes and macrophages are also believed to be the predominant cellular component in a number of cell-mediated immune responses including granuloma formation. The monocytes and macrophages are also known to be phagocytic and because they express Fc receptors for immunoglobulin G, they are major participants in antibody-dependent cellular cytotoxicity reactions (ADCC).

Human AKM also have an ability to recognize and kill tumor targets in vitro that is independent of antibody and may be augmented by such agents as interferon and muramyl dipeptide. Monocytes and macrophages are major components of the cellular infiltrate of both rodent and human tumors; in vitro studies using tumor-associated macrophages from both human and rodent tumors indicate that these cells can be activated to tumoricidal activity with various biological response modifiers. The reproducible in vitro activity of human blood monocytes, in the suspension culture system as described herein, is, of course, indicative of clinical utility.

The present invention is the first to demonstrate clinical feasibility and efficacy of AKM therapy.

As shown in Table II a number of technical and logistic difficulties relevant to the handling of human blood monocytes in the AKM protocol setting have now been solved. A new technique is described herein for isolating highly purified blood monocytes in large numbers by a combination of two blood component separation techniques: cytapheresis (Stevenson et al, Plasma Ther Transfus. Technol. 4:57–63. 1983, Fenwal Laboratories, Deerfield, Ill.), and counter-current centrifugal elutriation (Stevenson, Methods in Enzymology:Immunochemical Techniques, Part G. NY:Academic Press. Beckman Laboratories, Palo Alto, Calif.). Using a combination of these techniques, in accordance with the present invention, it has now been possible to obtain greater than 10⁹ human monocytes with a purity of 90 percent or more by a negative selection process that allows the cells to remain in suspension. The cells thus obtained are sterile and devoid of antibiotics or any toxins. Utilizing the methodology described herein supra, sufficient autologous monocytes from a single patient are obtained to demonstrate a significant clinical effect. Moreover, the ability to "home" these tumoricidal cells to the site of tumor burden has also been demonstrated in patients with peritoneal colorectal carcinomatosis (Table III-FIG. 5).

Peritoneal-colorectal carcinomatosis (PCC) disease represents a metastatic form of colon cancer and is universally fatal.

TABLE II

AKM Therapy

A. Techniques for obtaining purified effector monocytes identified; counter-current centrifugal elutriation.
B. Monocyte purification and activation techniques leave cells pyrogen, pathogen and toxin free.
C. Purified, clinical-grade monocyte activating substances (gamma IFN) available.
D. FDA approval for purified gamma interferon activated monocytes—granted.
E. Capable of culturing monocytes in suspension without antibiotics, animal sera or other sensitizing agents.
F. Mechanism for obtaining enough monocytes for clinical effect identified; counter-current centrifugal elutriation.
G. Autologous monocytes can be used in an AKM setting.
H. Mechanism for "homing" activated monocytes to sites of patient tumor burden identified: the peritoneal colorectal carcinomatosis.
I. In vitro testing of monocyte cytotoxicity against various human tumor cell types—ongoing.

No effective therapy presently exists. It is believed that the disease tends to metastasize to distant organs (such as lung and bond) in the late stage and frequently kills the patient by direct local extension into the viscera. This tendency to remain localized suggests the possibility that local elimination of this metastatic disease may greatly improve the length and quality of patient life. Previous studies with these patients in which Tenckhoff catheters have been inserted into the peritoneal space for the instillation of 5 fluorouracil ("5-FU bellywash" protocol), (Sugarbaker, Principles and Practice of Oncology. Philadelphia: Lippinicott Co., 1982) have provided an excellent clinical background for the direct deposition of tumoricidal leukocytes into the site of tumor burden in these patients.

Figure 5:
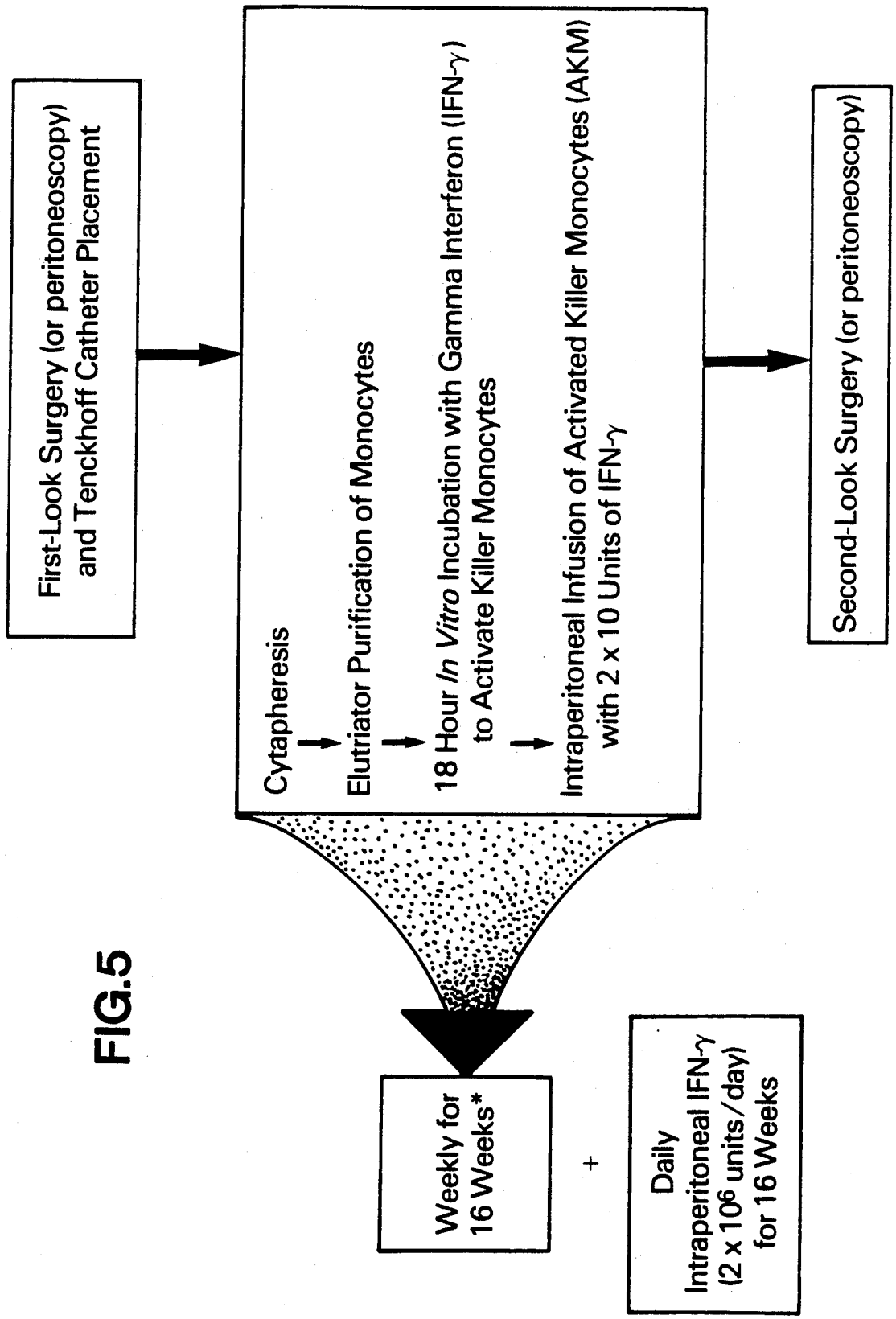
FIG. 5 shows a flow sheet of procedures involved in the AKM protocol for peritoneal colorectal carcinomatosis.

The AKM protocol for peritoneal colorectal carcinomatosis, in accordance with the present invention, is conducted at the National Cancer Institute, Bethesda, Md. As shown in FIG. 5, patients with a diagnosis of peritoneal colorectal carcinomatosis are referred to the National Cancer Institute for debulking surgery to render the patients as disease-free as is surgically possible, coupled with the insertion of a Tenckhoff catheter which communicates with the peritoneal space. Immediately following surgery, the patient received intraperitoneal infusion of approximately 500 to 900 million AKM. These cells are obtained by a 2-hour cytapheresis procedure followed by purification of the monocytes by counter-current centrifugal elutriation.

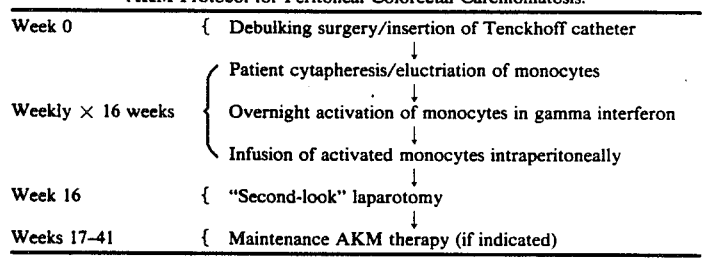

TABLE III

| AKM Protocol for Peritoneal Colorectal Carcinomatosis. | |
|---|---|
| Week 0 | { Debulking surgery/insertion of Tenckhoff catheter ↓ |
| Weekly × 16 weeks | ⎧ Patient cytapheresis/eluctriation of monocytes ↓<br>⎨ Overnight activation of monocytes in gamma interferon ↓<br>⎩ Infusion of activated monocytes intraperitoneally ↓ |
| Week 16 | { "Second-look" laparotomy ↓ |
| Weeks 17–41 | { Maintenance AKM therapy (if indicated) |

Following this, the purified monocytes are cultured in suspension overnight in gamma interferon (Genentech) at a concentration of 1000 U/ml. After overnight (about 12–16 hours) activation in gamma interferon, the AKM are infused into the peritoneal space via the Tenckhoff catheter. In addition, the patient receives a 2-liter infusion of peritoneal lavage fluid such as Impersol, (Travenol Laboratories, Deerfield, Ill.) to allow for the maximal distribution of the patient's AKM throughout the peritoneal space. In order to determine with certainty the patient's response to this form of therapy, a "second-look" laparotomy at the conclusion of 16 weeks of AKM therapy is conducted. Patients who are found to have a complete or partial response to AKM therapy are then offered a 6-month maintenance AKM therapy regimen.

Clinical Observations Regarding the AKM Protocol

Initially, two PCC patients were treated in the monocyte AKM protocol at the National Cancer Institute at the Biological Therapeutics and Surgery Branches. Both patients were remarkably similar in the nature of their disease and their response to AKM therapy. Both were white females, 38 and 41 years of age; one had a diagnosis of peritoneal colorectal carcinomatosis for 12 months, the other for 6 months. Both patients were without evidence of distant metastatic disease and neither patient had any other serious illnesses. Their functional status was excellent. Both patients had severe involvement of the peritoneal surfaces with cancer; virtually no aspect of the parietal peritoneum was spared. However, both patients had visibly less metastatic disease on the small intestine than elsewhere. Attempts to remove as much grossly visible disease as possible were successful. One patient required removal of a large segment of the colon in order to dissect away the malignancy. The other patient required removal of the spleen for the same purpose.

Both patients tolerated the AKM therapy remarkably well. As has been learned from the second patient, this therapy is safely performed in the outpatient department following the patient's recovery from the initial debulking surgery. Typically, the patients arrive one morning in the cytapheresis unit outpatient department and undergo a 2-hour cytapheresis procedure to remove between 5 and $9 \times 10_9$ leukocytes. Following this procedure they are sent home, and that afternoon and evening the patients' monocytes are purified by elutriation and placed in suspension culture with gamma interferon (1000 U/ml). The next morning, the patients return to the outpatient department to receive the infusion of their AKM along with 2 liters of additional intraperitoneal Impersol; this infusion generally takes approximately 30 minutes. The patients then return home with oral analgesics and Tylenol. Generally, within 4 to 6 hours of the infusion of the AKM, the patients note the onset of a low-grade fever (consistently less than 101° F.) and a low-grade abdominal pain. The fever is manageable with Tylenol, and the pain is usually manageable with oral analgesics (occasionally patients have received parenteral narcotics in the outpatient department if the pain was too severe). Within 12 hours, both the low-grade fever and abdominal pain had generally subsided, and both patients had spent the rest of the week performing their normal daily activities. In both patients, a low-grade granulocytopenia after the first 4 to 7 cytapheresis procedures (total leukocyte count approximately 3,500) is noted; at this juncture, the frequency of the AKM treatments is adjusted to once every other week with normalization of the peripheral leukocyte count.

Midway through the protocol, the trafficking pattern of the intraperitoneally infused Akm by prelabeling them with $^{111}$Indium is analyzed. FIG. 6 shows the typical distribution of the $^{111}$Indium-labeled AKM throughout the peritoneal space. The distribution is homogeneous with the few patchy areas of decreased uptake shown at second-look surgery to be due to postoperative adhesions. When interpretable images from these patients up to 5 days after intraperitoneal infusion of $^{111}$In-labeled monocytes is obtained, the evidence indicates that these cells do not traffic outside of the peritoneal space. Instead, they appear to become incorporated in the cellular matrix of the peritoneum, most likely transforming into tissue macrophages.

Both of the above-cited patients have undergone the "second-look" laparotomy staging procedure. Both were found to have normalization of the majority of the surface of their peritoneum including the sites most heavily infiltrated with tens of thousands of metastatic lesions at the first surgery. Neither of the patients were found to have any bulky lesions of the colon or the viscera, nor were they found to have distant metastases. However, they both had very small amounts of progressive disease (PD) in places which were restricted (predominantly by peritoneal adhesions) from access to the monocytes. These patients were rendered disease-free by removing the adhesions, exposing these areas, and surgically excising the lesions at operation (O) (all <1 cm.). They were thus designated as having an "O-PD" status. Both patients then went on to receive maintenance therapy following recuperation from the second-look laparotomy procedure. Both patients have remained free of relapse for over three years. As summarized in Table IV, four additional PCC cancer patients have been treated with AKM therapy; two continue to enjoy freedom from local relapse for over two years.

The results noted above clearly indicate that immunotherapy of peritoneal colorectal carcinomatosis with AKM is a feasible and efficacious procedure. In order to obtain maximal antitumor effect the AKM can also be combined with such factors as natural killer lymphocytes, antigen-specific killer T lymphocytes, B-cells and the like. Such "combination activated leukocyte therapy" can replace, supplement, mimic or reconstruct the natural immunologic system.

Of course, the availability of in vitro cultured, autologous, AKM in suspension opens a new vista for immunotherapy and/or fortification and supplementation of immune regulatory system in the mammals where such system has been adversely effected due to immune dysfunction.

TABLE IV

RESULTS OF SEVEN PCC[a] PATIENTS TREATED ON THE AKM[b] PROTOCOL

| AGE/SEX | STIMULATOR | TOXICITIES | RESULTS | FREEDOM FROM LOCAL RELAPSE |
|---|---|---|---|---|
| 44/F | nIFN γ[1] | Tmax = 101 peritoneal irritation (grade 2)[c] | O-PD[2] | 3.5 yrs. post-therapy |
| 41/F | nIFN γ | Afeb.: peritoneal irritation (grade 1):1 episode-bacterial | O-PD | 3.0 yrs. post-therapy |

TABLE IV-continued

RESULTS OF SEVEN PCC[a] PATIENTS TREATED ON THE AKM[b] PROTOCOL

| AGE/SEX | STIMULATOR | TOXICITIES | RESULTS | FREEDOM FROM LOCAL RELAPSE |
|---|---|---|---|---|
| 52/M | nIFN γ | peritonitis Afeb.: peritoneal irritation (grade 1) episode-bacterial peritonitis | I-PD[3], 8 cycles | |
| 42/F | nIFN γ | Afeb.: peritoneal irritation: (grade 1) | I-PD, 8 cycles | |
| 46/M | nIFN γ | Tmax = 100: peritoneal irritation (grade 1) epidose-bacterial peritonitis | 1 lung metastasis post-therapy, no clinical peritoneal disease | 2.5 yrs. post-therapy |
| 31/F | rIFN γ[4] | Tmax = 100: peritoneal irritation (grade 2) | O-PD | 2.0 yrs. post therapy |
| 38/M | rIFN γ | Afeb.: peritoneal irritation (grade 0) | SD[5], 16 cycles | |

[a]PCC, peritoneal colorectal carcinomatosis; [1]nIFN γ, natural interferon γ;
[b]AKM, Activated Killer Monocytes; [2]O-PD, small areas of progressive disease found at 2nd surgery (in areas to which monocytes had limited access)- Pt. rendered surgically disease-free; [3]I-PD, peritoneal progressive disease (surgically inoperable); [4]rIFN γ, recombinant interferon γ; [5]SD, stable disease.
[c]Peritoneal irritation grading system: 0 = none; 1 = manageable with oral analagesics; 2 = requiring parenteranarcotics; 3 = requiring intravenous fluids and nasogastric suction.

It is understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A method of producing activated killer monocytes, comprising the steps of:

(a) isolating purified human monocytes by elutriation in a serum free medium in polypropylene containers; and (b) converting the monocytes obtained in step (a) with an effective amount of gamma interferon to produce clinical grade activated killer monocytes.

2. A method of treating colorectal cancer in patients in need of immunotherapy, comprising peritoneally administering to said patient an immunotherapeutic effective amount of activated killer monocytes produced by the method of claim 1.

* * * * *